United States Patent
Cervenka et al.

(10) Patent No.: US 8,829,241 B2
(45) Date of Patent: Sep. 9, 2014

(54) CONTINUOUS CRYSTALLISATION PROCESS OF IODINATED PHENYL DERIVATIVES

(75) Inventors: Jan Cervenka, Oslo (NO); Khalid Hussain, Oslo (NO); Arne W. Aabye, Oslo (NO)

(73) Assignee: GE Healthcare AS, Oslo (NO)

( * ) Notice: Subject to any disclaimer, the term of this patent is extended or adjusted under 35 U.S.C. 154(b) by 550 days.

(21) Appl. No.: 11/996,985

(22) PCT Filed: Jul. 28, 2006

(86) PCT No.: PCT/NO2006/000288
§ 371 (c)(1),
(2), (4) Date: Jan. 28, 2008

(87) PCT Pub. No.: WO2007/013815
PCT Pub. Date: Feb. 1, 2007

(65) Prior Publication Data
US 2008/0214867 A1    Sep. 4, 2008

(30) Foreign Application Priority Data
Jul. 29, 2005 (NO) .................................. 20053687

(51) Int. Cl.
| | | |
|---|---|---|
| *C07C 233/05* | (2006.01) | |
| *C07C 233/65* | (2006.01) | |
| *C07B 63/00* | (2006.01) | |
| *C07C 231/24* | (2006.01) | |
| *C07C 17/392* | (2006.01) | |

(52) U.S. Cl.
CPC ............... *C07C 231/24* (2013.01); *C07B 63/00* (2013.01); *C07C 17/392* (2013.01)
USPC ........................................ 564/158; 424/9.452

(58) Field of Classification Search
USPC ........................................ 564/153; 424/9.452
See application file for complete search history.

(56) References Cited

U.S. PATENT DOCUMENTS

| | | | |
|---|---|---|---|
| 6,469,208 B1 * | 10/2002 | Villax et al. .................. | 564/153 |
| 6,646,171 B2 * | 11/2003 | Cervenka ...................... | 570/177 |
| 2010/0069669 A1 * | 3/2010 | Homestad .................... | 564/153 |

FOREIGN PATENT DOCUMENTS

| | | |
|---|---|---|
| JP | 2004-223451 | 8/2004 |
| WO | 99/18054 | 4/1999 |
| WO | 02/083623 | 10/2002 |

OTHER PUBLICATIONS

PCT/N02006/000288 Int'l Search Report/Written Opinion dated Nov. 2006.

* cited by examiner

*Primary Examiner* — Shailendra Kumar

(57) ABSTRACT

The invention describes a process for the purification of iodinated aryl compounds where the purification is performed by continuous crystallization of a crude product in a solvent with addition of anti-solvent. The continuous crystallization process is performed in one or more crystallizers at a temperature up to the boiling point of the content of the crystallizer.

25 Claims, No Drawings

CONTINUOUS CRYSTALLISATION PROCESS OF IODINATED PHENYL DERIVATIVES

This application is a filing under 35 U.S.C. 371 of international application number PCT/NO2006/000288, filed Jul. 28, 2006, which claims priority to application number 20053687 filed Jul. 29, 2005, in Norway the entire disclosure of which is hereby incorporated by reference.

TECHNICAL FIELD OF INVENTION

The invention relates to a process for the purification by crystallisation of iodinated aryl compounds such as iodinated X-ray contrast agents which allows for purification in an efficient and safe manner at a low cost. The invention relates in particular to industrial scale processes.

DESCRIPTION OF RELATED ART

A vast number of iodinated aryl compounds are known from the state of art. Of these, triiodinated phenyl derivatives are commonly used as X-ray contrast agents. Triiodinated phenyl compounds, containing three iodine atoms in meta positions to one another in the phenyl ring and various substituents at one or more of the non-iodine substituted phenyl carbons, are frequently achieved in multiple conformations with steric hindrance to transitions between such conformations. The so-called dimeric compounds, which contain two iodophenyl groups linked via a linking group such as an optionally substituted alkylene bridging group, are particularly constrained by the bulky substituents.

In the final step of the primary production process, the crude product containing the iodinated aryl compounds such as iodophenyl compounds has to be purified. A common system for purification is purification by crystallisation. To promote the crystal growth kinetics, the crystallisation needs to take place at elevated temperature. The crystallisation is also promoted by high supersaturation. However, high supersaturation may result in limited purity of the crystallised compounds. The crystallisation process is very demanding in terms of time and equipment size and will take several days, to perform. The crystallisation step is often a bottleneck in industrial scale processes.

The crystallisation is performed as batch processes. The batch size in industrial scale is usually from several hundred kilos and up to several tons and demands crystallisation equipment of considerable size. Many attempts have therefore been made to accelerate the process.

EP 747 344 A1 discloses purification and crystallisation of iopamidol by refluxing the solution at atmospheric pressure.

WO 99/18054 discloses a batch process for the crystallisation of e.g. triiodophenyl group containing compounds by effecting the crystallisation under elevated pressure.

Various solvent systems are proposed to provide proper saturation or supersaturation of the product in the solvent when using batch crystallisation processes, see e.g. U.S. Pat. No. 4,250,113, EP 747 344, GB 2 280 436, WO 98/08804, WO 99/18054, WO 02/083623 and WO2005/003080.

In addition to searching for processes that are easier to perform and less demanding with regards to time consumption and need for costly equipment, the main challenge in the production process is to meet the criteria for purity as set by the Health Authorities for X-ray contrast agents to be suitable for in vivo administration e.g. for intravenous administration. For example, the European Pharmacopea specifies the purity for the dimeric compound iodixanol (1,3-bis(acetamino)-N,N'-bis[3,5-bis-(2,3-dihydroxypropylaminocarbonyl)-2,4,6-triiodophenyl)]-2-hydroxypropane) which is the active pharmaceutical ingredient (API) of the commercial X-ray contrast agent Visipaque™ and for the monomeric compound iohexyl (5-(acetyl(2,3-dihydroxypropyl)amino)N,N'-bis(2,3-dihydroxypropyl)-2,4,6-triiodobenzene-1,3-dicarboxamide)) which is the active pharmaceutical ingredient (API) of the commercial X-ray contrast agent Omnipaque™ of not less than 98.0%.

It has now surprisingly been found that iodinated aryl compounds such as iodophenyl compounds can successfully be purified by a continuous crystallisation process.

SUMMARY OF THE INVENTION

In one embodiment the present invention provides a process for the purification of iodinated aryl compounds by continuous crystallisation of the corresponding crude product containing the compounds in a solvent, by addition of one or more anti-solvents during the process. Specifically, iodophenyl compounds such as those used as active pharmaceutical ingredients (API) in X-ray contrast agents for in vivo use can be produced by a continuous crystallisation process. By performing the crystallisation process as a continuous crystallisation process the yield per volume and time unit of the equipment is increased while the purity level of the crystallised iodinated compounds are maintained and may even be increased.

DETAILED DESCRIPTION OF THE INVENTION

In its broadest scope the invention relates to a process for the purification of iodinated aryl compounds where the purification is performed by continuous crystallisation of the compound from a crude product in a solvent with addition of anti-solvent.

By solvent is meant a liquid or a mixture of liquids wherein the compound is generally well soluble whereas by anti-solvent is meant a liquid or a mixture of liquids wherein the compound is less soluble and preferably significantly less soluble than in the solvent.

Various solvents and anti-solvents for the use in the crystallisation of iodinated aryl compounds are known from the prior art as discussed above. In the purification process of the invention, a mixture of anti-solvents can beneficially be employed in the process. Use of mixtures of anti-solvents will enable the generation of anti-solvents that have the desired properties with regard to solubility of the compound to be crystallised and the boiling point of the anti-solvent.

Alternatively, selection of one single anti-solvent for the use in the crystallisation process is also possible. Use of a single anti-solvent is usually preferred when this anti-solvent can fulfil the criteria mentioned for mixtures of anti-solvent.

The term anti-solvent in the further specification comprises a mixture of anti-solvents or a single anti-solvent and the term solvent comprises a single solvent or a mixture of solvents. In general, singular and plural forms are used interchangeably in this document.

Iodinated aryl compounds and in particular iodinated phenyl compounds (collectively denoted compound/compounds) for use as API in in vivo X-ray contrast agents are soluble in water and the X-ray contrast agents are usually provided commercially as aqueous solutions of the API. This class of compounds are usually sterically hindered organic compounds and a high input of thermal energy is needed for the compounds to adopt a conformation required by the crystalline structure. Hence, the thermal energy needed is provided by working at elevated temperatures up to the boiling point of the content of the crystallisers. The boiling point of the anti-solvents and the anti-solvents in mixture with the solution of the crude product to be crystallised should therefore be moderate, and at a temperature where the iodinated compound and other constituents of the crude product and the solvents are stable. Preferably the boiling point of the solvents and anti-solvents should be below 150° C. at ambient pressure, more preferably below 120° C., e.g. from 30° C. to 110° C. The crystallisation should be effected at a temperature below 200° C., preferably below 150° C. and particularly below 120° C. The crystallisation should be effected at ambient pressure or at elevated pressure e.g. at an overpressure of from 0.05 to 20 bar. In a preferred embodiment, the crystallisation should be performed at the boiling point or alternatively at a temperature slightly below the boiling point of the solution, i.e. the content of the crystalliser at the specific pressure used in the crystallisation process.

The anti-solvent should be fully mixable with the solution of the crude product. When the anti-solvent is added to the crude product in solution, a saturation or supersaturation of the crude product is created and the compound will crystallise from the solution, usually from a solution held at the boiling point or slightly below the boiling point of the content of the crystalliser.

The anti-solvents for the compound to be crystallised from the crude product is usually selected from alcohols, ketones, esters, ethers and hydrocarbons, especially alcohols, alcohol-ethers, ethers and ketones, e.g. $C_{2-5}$ alcohols. Examples of suitable anti-solvents include ethanol, n-propanol, isopropanol, n-butanol, i-butanol, sec-butanol, t-butanol, pentanols including isoamyl alcohol, acetone, ethyl-methyl ketone, formaldehyde, acetaldehyde, dimethyl ether, diethyl ether, methylethyl ether, tetrahydrofuran, ethylacetate, acetonitrile, dimethylsulphoxide, dimethylformamide, dimethylacetamide, benzene, toluene, xylene, n-hexane, cyclohexane, n-heptane, etc. and mixtures of these compounds. Especially preferred are $C_1$-$C_5$-monoalkylether of a $C_2$-$C_{10}$ alkylene glycol such as 1-methoxy-2-propanol, and 2-propanol.

The crude product is obtained from the primary production of the compounds. The primary production is a multistep synthetic procedure wherein the aryl group, e.g the phenyl group, is substituted by hydroxy alkyl and/or acylamino and/or alkylaminocarbonyl groups that are optionally further substituted by hydroxy groups, amino groups, ether groups and similar groups or the alkyl chains may contain oxo or thio groups. The aryl groups are further substituted by iodine atoms, for phenyl groups usually by three iodo atoms in meta positions to one another. Tri-iodinated phenyl compounds as well as dimers and multimers of such compounds and in particular non-ionic compounds thereof are as noted above useful as API of X-ray contrast media.

Examples of such momomers and dimers are diatrizoate, iobenzamate, iocarmate, iocetamate, iodamide, iodipamide, iodixanol, iohexyl, iopentol, ioversol, iopamidol, iotrolan, iodoxamate, ioglicate, ioglycamate, iomeprol, iopanoate, iophenylate, iopromide, iopronate, ioserate, iosimide, iotasul, iothalamate, iotroxate, ioxaglate, ioxitalamate, metrizamide, metrizoate, iobitritol, ioxaglic acid, iosimenol and other compounds from the state of art including monomers and dimers known from WO96/09285 and WO96/09282.

Several of the monomers and dimers listed above are the API of commercial X-ray contrast agents for example iohexyl of Omnipaque™, iopamidol of Isovue™, iomeprol of Iomeron™, iopromide of Ultravist™, iotrolan of Isovist™, iodixanol of Visipaque™ and iotribitrol of Xenetix™. These products are produced in high quantities and efficient and economic viable processes are continuously sought.

The products mentioned above and their manufacturing processes are known from the literature and from patent publications, e.g. from U.S. Pat. No. 4,364,921, U.S. Pat. No. 4,250,113, U.S. Pat. No. 5,349,085, U.S. Pat. No. 4,001,323, U.S. Pat. No. 4,352,788, U.S. Pat. No. 4,341,756 and U.S. Pat. No. 5,043,152.

Prior to the crystallisation the solution containing the crude product from the primary production can be further purified. Preferably, if the solution of the crude product contains amounts of salt, the solution can be fully or partially desalinated e.g. by treatment on ion exchange columns. Any solvents used during the chemical synthetic steps should also be reduced if necessary to an amount not interfering substantially with the crystallisation process.

The solution of the crude product may also be concentrated by the removal of parts of the solvent e.g. under vacuum and/or by azeotropic distillation. For example, the amount of water as solvent can vary from 5% to 100% by weight of the crude product, preferably below 50% by weight. When the crude product contain the compound iodixanol, about 20 weight % of water and optionally in addition 100 to 300 weight % of methanol relative to crude iodixanol is found to give good results when used as the crude product feeding stream to the crystalliser.

The crude product from the synthesis optionally pretreated as explained above is used as the feeding stream to the crystalliser. The crystalliser or crystallisation unit comprises one or more crystallisation tanks optionally equipped with a reflux condenser and at least one inlet for the feeding stream and one outlet for the product stream. The tank may further be equipped with a heater, e.g. as a jacket for temperature control and may also be equipped with a mixing device. Optionally the tank comprises further inlet and outlet openings e.g. for feeding of additional anti-solvents and/or for extracting samples. The feeding and the extraction is preferably performed by pumping liquid in and out, however other arrangements are also feasible like utilising the gravity force.

The crystallisation unit may further be equipped to enable pressurising the content of the crystallisers.

The crystalliser where the feeding of the crude product in solution is performed is preferably preloaded with a suitable amount of crystals of the product to be crystallised suspended in the solvent, e.g. water, and in one or more of the anti-solvents. The use of seed crystals will enhance the initial crystallisation process and promote the establishment of steady state conditions.

When commencing the crystallisation process the feeding stream comprising the solution of the crude product preferably pretreated as described above, is loaded into a crystalliser preferably equipped as described above and preloaded with a suspension of crystals. Concurrently with feeding of the solution of the crude product or alternatively slightly before or after the feeding of the solution of the crude product has commenced, the anti-solvent is fed to the crystalliser either through the same inlet or through a separate inlet.

The crude product in solution and the anti-solvent are fed into the crystalliser at constant rates. The crystallised compound of the product stream is withdrawn at constant rate as a suspension. The sum of the feeding rate of the crude product in solution (F1) and of the anti-solvent (F2) is usually equal to the amount of product withdrawn as the product stream (F3), in other words, F1+F2=F3 at steady state, to keep the volume load constant. The feeding rates will decide the residence time of the compound in the crystalliser. The residence time may be set according to the kinetic of the crystallising compound and the required production capacity. The optimal residence time in each crystalliser is dependent on the number and volume of crystallisers employed and must be optimised for each specific process.

The feeding rates F1 and F2 may be the same or different depending on the concentration of the compound and anti-solvent in the feeding streams.

A process is considered to be at steady state if the process variables do not change with time. The steady state is characterised by a particular solvent and anti-solvent content, temperature, mother liquid concentration, magma density and particle size distribution.

The crystallisation process is run using one or more crystallisers. Each crystalliser is preferably equipped with a reflux condenser so that the process can be performed under partial or total reflux. The crystallisers will usually be coupled in series, optionally with partial recycling of the product stream and mother liquor or crystals after filtration from a crystalliser to a previous crystalliser in the series. The overall solubility decreases from the first to subsequent crystalliser, e.g. by the addition of a balanced amount of anti-solvent to the crystallisers or changing the temperature to achieve optimum supersaturation in each crystalliser.

Although sufficient yield and purity of the compound can be achieved in one crystalliser only, it is generally preferable to run the process in two or more crystallisers. Hence, by using multiple crystallisers the ratio of anti-solvent/solvent content can be gradually increased so that almost the entire amount of the desired compound is crystallised from the mother liquor. The crystallisers may operate at the same or different temperature and pressure. It is important to control change in the anti-solvent/solvent content since a gradual increase in the ratio promotes the crystal growth and filterability of the crystallised compound as well as the purity of the crystalline compound.

As noted above, the residence time of the compound in the crystallisers will vary depending of the number of crystallisers, the change in the anti-solvent/solvent content from one crystalliser to the next and the rate of the crystal growth. Crystallisers in series are usually preferred and can be combined with at least one crystalliser where the temperature is reduced. The compound is continuously withdrawn from the crystalliser system as a product stream containing the crystallised compound as a suspension. The compound is isolated by filtration and washed if needed to remove remaining mother liquor and is dried if desired.

Alternatively, the process can be run as a combination of a continuous crystallisation process and a batch crystallisation process where the compound is mainly crystallised in the continuous crystallisation process before the remaining crystallisation is performed as a batch crystallisation process. It is also possible to perform the initial crystallisation in a batch crystallisation fashion and then to continue the crystallisation as a continuous crystallisation process, preferably in the same crystalliser. The purpose of this arrangement is to achieve a sufficient amount of crystals in the solution before switching to the continuous crystallisation mode. The continuous crystallisation process may be followed by a batch crystallisation from which the compound is withdrawn and if necessary or desirable is washed and dried before the compound is collected.

In a preferred embodiment the invention comprises a process for continuous crystallisation of iodixanol from water-methanol/2-propanol or water/1-methoxy-2-propanol solvent/anti-solvent system using one or multiple stirred tanks equipped with reflux condensers. The process is run at normal boiling temperature of the content of the crystalliser or higher temperatures when using elevated pressure.

In another preferred embodiment the invention comprises a process for continuous crystallisation of iohexyl from water-2-methoxyethanol/2-propanol solvent/anti-solvent system.

The process may be run as a fully continuous process or as a combination of continuous and batch crystallisers. The size of the continuous crystallisers and the residence time may be decided according to the kinetic of the crystallising compound and the required production capacity.

EXAMPLES

The invention will now be further described by the non-limiting examples. All % are in weight % if not specified otherwise.

Example 1

Continuous Crystallisation of Iodixanol from Methanol/Water/2-Propanol

Preparation of Seed Crystal Solution:

203 g of crystalline iodixanol of 98% purity was suspended in a mixture of 39 ml water, 600 ml methanol and 365 ml 2-propanol in a jacketed continuous crystalliser (1100 ml). The suspension was heated to the boiling temperature at atmospheric pressure with total reflux.

Continuous Crystallisation Process:

A crude product solution was made by dissolving the crude product, containing about 85% iodixanol, in a solvent mixture of 0.19 ml water/g crude product and 1 ml methanol/g crude product. This solution was pumped into the crystalliser at a constant volumetric flow (F1). A solvent mixture, consisting of 53 volume % methanol and 47 volume % 2-propanol, was also pumped into crystalliser at a constant flow rate (F2). The ratio F1/F2 was given by the desired amount of the respective solvent in proportion to the crude product. In this experiment the amount of solvents were set to 0.19 ml water/g crude product, 3.0 ml methanol/g crude product and 1.8 ml 2-propanol/g crude product. The total flow into the crystalliser (F1+F2) was adjusted according to a desired residence time. The suspension flow from the continuous crystalliser was collected in a stirred batch crystalliser that was kept at boiling temperature (with total reflux).

With a residence time of 5 hours, the constant level of the mother liquor concentration in the continuous crystalliser was reached after 24 hours operation. The experiment was finished at about 29 hours after start. At this time the concentration of the UV-absorbing substance (at 244.5 nm) in the mother liquor was 9.8% in the continuous crystalliser and 5.2% in the batch crystalliser. The purity of the compound was 98.4%.

The throughput per crystalliser volume and time unit of the continuous crystallisation process was 36 kg iodixanol/$m^3$ hour. In the corresponding batch process a typical throughput is 3 kg iodixanol/$m^3$ hour.

Example 2

Continuous Crystallisation of Iodixanol from Water/1-Methoxy-2-Propanol

Preparation of Seed Crystal Solution:

240 g crystalline iodixanol of 98% purity was suspended in a mixture of 46 ml water and 933 ml 1-methoxy-2-propanol in a jacketed continuous crystalliser (1100 ml). The suspension was heated to the boiling temperature at atmospheric pressure with total reflux.

Continuous Crystallisation Process:

A crude product solution was made by dissolving the crude product, containing about 85% iodixanol, in a solvent mixture of 0.20 ml water/g crude product and 0.84 ml 1-methoxy-2-propanol/g crude product. This solution was pumped into the pre-seeded crystalliser at a constant volumetric flow (F1). The total amount of 1-methoxy-2-propanol was adjusted by adding 1-methoxy-2-propanol to the crystalliser at a constant flow rate (F2). The ratio F1/F2 was given by the desired amount of the 1-methoxy-2-propanol in proportion to the crude product. In this experiment the total amount of 1-methoxy-2-propanol was set to 4.0 ml/g crude product. The total flow into the crystalliser (F1+F2) was adjusted according to a desired residence time. The suspension flow from the continuous crystalliser was collected in a stirred batch crystalliser that was kept at boiling temperature (with total reflux).

With a residence time of 8 hrs the constant level of the mother liquor concentration in the continuous crystalliser was reached after 20 hours operation. The experiment was finished at about 44 hours. At this time the concentration of the UV-absorbing substance (at 244.5 nm) in the mother liquor was 4.9% in the continuous crystalliser and 3.9% in the batch crystalliser. The purity of the compound was 98%.

The throughput per crystalliser volume and time unit of the continuous crystallisation process was 26 kg iodixanol/m$^3$ hour. In the corresponding batch process a typical throughput is 4 kg iodixanol/m$^3$ hour.

Example 3

Continuous Crystallisation of Iohexyl from 2-Methoxyethanol/Water/2-Propanol

The crystallisation was performed in a baffled stirred crystalliser of 1100 ml working volume. The crystalliser was heated through a heating jacket and equipped with a condenser, an inlet for crude product solution, another one for the anti-solvent, and an outlet for the product removal. The additions and product removal were operated with peristaltic pumps.

The continuous crystallisation process was initiated in the crystalliser preloaded with 1000 ml 2-propanol, 70 ml 2-methoxyethanol and 210 g of iohexyl crystals. The continuous process was performed by pumping in the crude product solution (1.47 ml/min, approximately 60° C.) through one inlet, and 2-propanol (5.87 ml/min, ambient temperature) through the other inlet into the boiling suspension. The crystallising suspension was continuously withdrawn from the crystalliser at the rate of 8 ml/min, keeping the suspension volume constant. The residence time of the suspension was 2.5 hours.

The crude product solution was made by dissolving the crude product containing 96.6% iohexyl in a mixture of 2-methoxyethanol and water. The solution consisted of 70.7% crude product, 0.85% water and 28.4% 2-methoxyethanol.

After 23 hours run (approximately 9 times the residence time) the system was considered to be at steady state. The concentration of the UV-absorbing substance (at 245 nm) in the mother liquor was 2.6%. The purity of the filtered and washed crystalline product was 99.0%.

The throughput per crystalliser volume and time unit of the continuous crystallisation process was 85 kg iohexyl/m$^3$ hour. In the corresponding batch process a typical throughput is 9 kg iohexyl/m$^3$ hour.

Example 4

Continuous Crystallisation of Iodixanol in Water/1-methoxy-2-Propanol

The crystallisation was performed in a baffled stirred crystalliser of 1100 ml working volume. The crystalliser was heated through a heating jacket and equipped with a condenser, an inlet for crude product solution, another one for the anti-solvent, and an outlet for the product removal. The additions and product removals were operated with peristaltic pumps.

The continuous crystallisation process was initiated in the crystalliser preloaded with 700 ml 1-methoxy-2-propanol, 80 ml water and 400 g of iodixanol crystals. The continuous process was performed by continuously pumping the crude product solution (1.26 ml/min at approximately 80° C.) through one inlet, and 1-methoxy-2-propanol (1.02 ml/min at ambient temperature) through another inlet into the boiling suspension. The crystallising suspension was continuously withdrawn from the crystalliser at the rate of 2.5 ml/min, keeping the suspension volume constant. The residence time of the suspension was 8 hours.

The crude product solution was made by dissolving the crude product containing 96.7% iodixanol in a mixture of 2-methoxyethanol and water. The solution consisted of 49.7% of crude product, 10.1% water and 40.2% 2-methoxyethanol.

After 48 hours run (approximately 6 times the residence time) the system was considered to be at steady state. The concentration of the UV-absorbing substance (at 244.5 nm) in the mother liquor was 5.5%. The purity of the filtered and washed crystalline product was 98.7%.

The throughput per crystalliser volume and time unit of the continuous crystallisation process was 46 kg iodixanol/m$^3$ hour. In the corresponding batch process a typical throughput is 6 kg iodixanol/m$^3$ hour.

What is claimed is:

1. A continuous crystallization process for the purification of a crude product comprising iodinated phenyl compounds comprising the following steps:
    i) feeding a solution comprising said crude product in a solvent into a crystallizer;
    ii) feeding an anti-solvent into said crystalizer;
    iii) achieving optimum supersaturation by either balancing the amount of said anti-solvent fed to the crystallizer or adjusting the temperature of the crystallization process;
    iv) withdrawing crystallized iodinated phenyl compound as a suspension; and
    v) establishing steady state conditions wherein:
        said solution comprising said crude product and said anti-solvent are fed into the crystallizer at constant rates;
        said crystallized iodinated phenyl compound is withdrawn as a suspension at constant rate; and
        the volume load of said crystallizer is kept constant.

2. Process of claim 1 wherein the iodinated phenyl compounds are triiodinated phenyl derivatives.

3. Process of claim 2 wherein the iodinated phenyl compounds are water soluble, crystalline triiodinated phenyl derivatives.

4. Process of claim 1 wherein the iodinated phenyl compounds are selected from iohexol, iopamidol, iomeprol, iopromide, iotrolan, iodixanol and iotribitrol.

5. Process of claim 1 wherein the continuous crystallization process is performed at a temperature up to the boiling point of the content of the crystallizer.

6. Process of claim 1 wherein the process is performed up to the boiling point at ambient pressure.

7. Process of claim 1 wherein the process is performed up to the boiling point at elevated pressure.

8. Process of claim 7 wherein the elevated pressure is 0.05 to 20 bar.

9. Process of claim 1 wherein the process is performed at the boiling point or at a temperature slightly below the boiling point of the content of the crystallizer at the specific pressure.

10. Process of claim 1 wherein the process is performed under reflux.

11. Process of claim 1 wherein the process is performed using one or more crystallizers.

12. Process of claim 1 wherein the feeding rates of the crude product in the solvent and of the anti-solvent are decided by the residence time of the compound in the crystallizers.

13. Process of claim 1 further comprising batch crystallization.

14. Process of claim 1 wherein continuous crystallization is performed in one or more crystallizers and with a final batch crystallization.

15. Process of claim 1 wherein the crystallizer is preloaded with crystals of the compound being crystallized.

16. Process of claim 1 wherein the purification is performed by crystallization with addition of a single anti-solvent.

17. Process of claim 1 wherein the purification is performed by crystallization with addition of an anti-solvent mixture.

18. Process of claim 16 wherein the anti-solvent comprises compounds of the group comprising alcohols, ketones, esters, ethers and hydrocarbons.

19. Process of claim 18 wherein the anti-solvent comprises $C_1$-$C_5$-monoalkylether of a $C_2$-$C_{10}$ alkylene glycol.

20. Process of claim 19 wherein the anti-solvent comprises 1-methoxy-2-propanol.

21. Process of claim 18 wherein the anti-solvent comprises a $C_2$-$C_5$-alcohol.

22. A process of claim 21 wherein the $C_2$-$C_5$-alcohol comprises 2-propanol.

23. Process of claim 1 wherein the solvent comprises water.

24. Process of claim 23 wherein the solvent comprises methanol.

25. Process of claim 23 wherein the solvent comprises 2-methoxy-ethanol.

\* \* \* \* \*